United States Patent
Carlsson et al.

[11] Patent Number: 6,068,860
[45] Date of Patent: May 30, 2000

[54] PHARMACEUTICAL FORMULATION

[75] Inventors: Anders Nils-Erik Carlsson; Johan Georg Harmenberg; Bengt Göran Herslöf, all of Stockholm; Ann Harriet Margareta Kristofferson, Södertälje; Stefan Karl Lundquist, Skärholmen, all of Sweden

[73] Assignee: Astra Aktiebolag, Sodertalje, Sweden

[21] Appl. No.: 08/602,784

[22] PCT Filed: Feb. 2, 1996

[86] PCT No.: PCT/SE96/00123

§ 371 Date: Mar. 8, 1996

§ 102(e) Date: Mar. 8, 1996

[87] PCT Pub. No.: WO96/24359

PCT Pub. Date: Aug. 15, 1996

[30] Foreign Application Priority Data

Feb. 6, 1995 [WO] WIPO ............... PCT/SE95/00112

[51] Int. Cl.[7] .................................................. A01N 59/26
[52] U.S. Cl. ........................................ 424/601; 514/178
[58] Field of Search ........................... 424/601; 514/178

[56] References Cited

U.S. PATENT DOCUMENTS

| | | | |
|---|---|---|---|
| 4,512,978 | 4/1985 | Inwood | 424/145 |
| 4,610,868 | 9/1986 | Fountain et al. | 424/1.1 |
| 5,227,165 | 7/1993 | Domb et al. | 424/450 |

FOREIGN PATENT DOCUMENTS

| | | |
|---|---|---|
| 636255 | 4/1993 | Australia . |
| 0009842 | 4/1980 | European Pat. Off. . |
| 9842 | 4/1980 | European Pat. Off. . |
| 0249561 | 12/1987 | European Pat. Off. . |
| 0350287 | 1/1990 | European Pat. Off. . |
| 8905152 | 6/1989 | WIPO . |
| 9503805 | 9/1995 | WIPO . |

OTHER PUBLICATIONS

The Merk Index, 10th Edition, p. 607, entry 4135, Apr. 24, 1984.

Jocam, U.E.; Load—Liposomen topisch appliziert, Pharmaceutische Zeitung Nr. 33, Aug. 13, 1992.

Schreier, H.; Liposomes and iosomes as topical drug carriers: dermal and transdermal drug delivery, Journal of Controlled Release 30 (1994), 1–15.

Spruance, S.L.; Topical therapy of Mucocutaneous Herpesvirus Infections, International Antiviral News, Jun. 1994.

Alenius, S, et al; Therapeutic Effects of Foscarnet Sodium and Acyclovir on Cutaneous Infections Due Herpes Simplex Virus Type 1 in Guinea Pigs, J. Inf. Dis. 1982, vol. 145, No. 4, Apr. 1982.

The Human Herpesviruses, ed. Roizman et al. 1993, Whitely Richard et al.; The Epidemiology and Clinical Manifestations of Herpes Simplex Virus Infections.

(List continued on next page.)

*Primary Examiner*—Dwayne C. Jones
*Attorney, Agent, or Firm*—White & Case L.L.P.

[57] ABSTRACT

The invention relates to a pharmaceutical composition for topical administration comprising a combination of foscarnet and an antiinflammatory glucocorticoid, in admixture with a carrier based on galactolipids and a polar solvent. The pharmaceutical composition can be used in a prophylactic and/or curative treatment of herpesvirus infections in mammals including man.

The invention also relates to the use of said pharmaceutical composition in the manufacture of a medicament for said prophylactic or curative treatment.

16 Claims, 3 Drawing Sheets

OTHER PUBLICATIONS

Kristofferson, A. et al.; Limited Efficacy of Inhibitors of Herpes Simplex Virus DNA Synthesis in Murine Models of Recrudescent Disease, J. Gen. Virol. (1988), 69, 1157–1166.

From Chemical Abstracts, vol. 112, No. 4; Loftsson, T.; Effect of choline esters and oleic acid on the penetration of acyclovir, estradiol, hydrocortisone, nitroglycerin, retinoic acid and trifluorothymidine across hairless mouse skin in vitro, Acta Pharm. Nord. (1989), 1(5), 279–86.

From Chemical Abstracts, vol. 112, No. 4, (Dissertation): Choi, Hoo Kyun; Enhanced transdermal delivery of propanolol, hydrocortisone, acyclovir and peptide–type drugs.

Foley: Permeability of liposomes composed of binary mixtures of MGDG and DGDG, Biochem. Ciophys. Acta 959 (1988).

Biosynthesis and function of plant lipids, ed. Thompson et al.; Sprague, S., et al; Bilayer and non–bilayer configurations of mixtures of isolated chloroplast membrane lipids.

PHARMACEUTICAL FORMULATION

FIELD OF THE INVENTION

The present invention relates to a pharmaceutical composition for topical administration comprising foscarnet in combination with an antiinflammatory agent in a pharmaceutically acceptable carrier. The composition can be used in the prophylactic and curative treatment of infections caused by herpesvirus and other viruses replicating in the skin, as well as on other cutaneous lesions on which the combination of foscarnet and antiinflammatory agent has an effect.

BACKGROUND OF THE INVENTION

Herpesvirus infections in humans can be caused by different human herpesviruses, the most common being herpes simplex virus and varicella-zoster virus. There are also many animal herpesviruses.

Following a primary infection with herpes simplex virus or varicella-zoster virus, the virus establishes latency in the sensory nerve cells for the rest of the patient's life and can subsequently be reactivated repeatedly. Following a reactivation in the nerve cell, the virus is transported through the nerves to the skin and subsequently a lesion develops. One characteristic of herpesvirus infection is the inflammation which follows immediately upon an outbreak of virus replication. The inflammation contributes to all symptoms associated with herpesvirus recurrence including redness, swelling, itching and pain as well as lesions.

Herpes simplex viruses can be divided into two serotypes, HSV type 1 (HSV-1) and type 2 (HSV-2), the clinical manifestations of which range from benign self-limiting orofacial and genital infections to potentially life threatening conditions such as encephalitis and generalized neonatal infections.

Oral-facial HSV infections are primarily caused by HSV-1. Following a primary infection in childhood the virus becomes latent. After reactivation a recurrent oral-facial HSV infection develops, which is more commonly known as a cold sore. About half of the patients experience prodromal symptoms such as pain, burning or itching at the site of the subsequent lesions. The condition is generally rapidly self-limiting and a typical episode will heal in around 10 days from the first symptoms. Viral replication in the lip is initiated early and maximum virus load is attained 24 hours after the onset of the reactivation. The virus concentration is then dramatically reduced and typically virus cannot be isolated 70–80 hours after the onset.

The clinical presentation of genital HSV infections is similar to the oral-facial infections with some important exceptions. Genital HSV infections are most often caused by HSV-2 and following the primary infection the virus will latently infect sensory or autonomic ganglions. Reactivation will produce the local recurrent lesions on or near the genitals that are characteristic of the herpes infection.

A primary infection with varicella-zoster virus (VZV) causes chicken-pox. Like HSV, VZV becomes latent following the primary infection and can be activated as herpes zoster later on in life. Zoster usually results in skin rash and intensive acute pain. In 30% of the patients, the pain can be prolonged and continue for weeks or months after the rash has cleared up.

HSV and VZV may, in addition to mucous or cutaneous manifestations, also cause keratitis in the eyes. This condition is also recurrent and may cause blindness.

There are a number of antiviral agents which are active against the human herpesviruses. There has, however, so far been limited clinical success in the treatment of recurrent herpesvirus infections.

Foscarnet, the hexahydrate of the trisodium salt of phosphonoformic acid or sodium phosphonoformate hexahydrate, is a well-known antiviral agent with a broad antiviral spectrum, acting by direct inhibition of viral DNA polymerase in herpes viruses and of viral reverse transcriptase in retroviruses. Foscarnet has been approved for clinical use for systemic, that is intravenous, treatment of CMV retinitis in AIDS patients. A side-effect of said treatment is a renal function impairment as well as other symptoms which can be tolerated in the treatment of a life-threatening condition but hardly in the treatment of benign, self-limiting recurrent HSV infections in immunocompetent patients.

When the herpes infection is limited to the skin or mucous membranes, topical therapy could be advantageous. This will reduce the exposure of the body for the active substance and allow higher drug concentrations which could make it possible to reach higher concentrations in the part of the skin where viruses replicate.

Although foscarnet has a proven activity against all human herpes virus in vitro, testing of foscarnet, applied topically, against recurrent herpes simplex virus infections in immunocompetent patients has only met with a moderate degree of success. The healing time of lesions upon such treatment is shortened with approximately one day. In said tests foscarnet was applied in a conventional cream formulation. A topical administration of foscarnet in a 3% formulation is known to cause irritation of mucous membranes or the skin in the genital region making the medical treatment painful. One purpose of this invention is, therefore, to find a composition of foscarnet that elicits a very low degree of tissue irritation in addition to a potent antiviral effect.

Clinical primary infections with human herpes simplex viruses differ in a number of important aspects from subsequently reactivated infections. The viral shedding period is longer in the primary infection (about 10 days in labial and 3 weeks in genital infection) compared with reactivated infection (3–4 days for both labial and genital infections). Following termination of the viral shedding period in primary infections the lesion will heal in a few days while in the case of reactivated infections, the inflammation continues after viral replication has ceased and the clinical symptoms will remain for another week.

Obviously a reduction of virus multiplication in itself will not substantially alter the clinical course of a recurrent herpes infection. It is, therefore, not surprising that antiviral drugs when tested in clinical trials show a more substantial effect against a primary infection as compared with reactivated infections, such as recurrent herpes labialis or genitalis. Because of the rapid self-limiting nature of the virus shedding period in recurrent HSV infection the improvement of only one day healing time obtained in clinical trials with antiviral drugs is not surprising.

Different antiinflammatory agents have been tested to treat the inflammation that accompanies the recurrent infection, but only with limited success. Traditionally, inflammatory conditions in the eye, such as keratitis, have been treated with steroids. Even though this type of compounds is known to potentially promote herpesvirus replication steroids have been used in severe cases, for instance to save the patients vision. This practice has been controversial. In summary, there has been little clinical success in the treatment of recurrent herpesvirus infections even with the most potent antiviral drugs. There is, thus, a great need for effective drugs and methods of treatment for recurrent herpes infections.

PRIOR ART

Jocham, U. E., Pharmaceutische Zeitung, Nr. 33, Aug. 13, 1992, pp. 28–34, describes the possible use of foscarnet-liposomes for a non-invasive treatment of herpes infections of the eye in AIDS patients. Said patients are today systemically treated owing to the strongly irritating effect of the antiviral. It is also stated that a local treatment of the skin with an active substance in a liposomal carrier will promote the penetration of the active substance through the stratum corneum of the skin and give a local enrichment of said active substance.

Schreier, H. et al., Journal of Controlled Release 30 (1994) pp. 1–15, is a review of dermal and transdermal drug delivery of substances encapsulated within liposomes and niosomes. It is concluded that liposomes and niosomes may become a useful dosage form for a variety of dermally active compounds, specifically due to their ability to modulate drug transfer and serve as nontoxic penetration enhancers. It is also reported that liposomes prepared from ceramides, that is sphingolipids, are more effective in penetrating into the skin than liposomes prepared from phospholipids. As a means to improve the treatment of cutaneous virus infections, specifically herpes simplex virus infections, the deposition of interferon-α liposomally formulated with skin lipids, that is mainly ceramides and cholesterol, was evaluated and shown to be delivered to deep skin layers.

Spruance, S. L., Topical therapy of mucocutaneous herpesvirus infections, International Antiviral News, Jun. 2, 1994, pp. 86–87, reports that the search for an effective topical treatment for recurrent herpes labialis in normal hosts has been hindered by suboptimal drug formulations and an inadequate appreciation of the need for early therapeutic intervention. Although a formulation of acyclovir in an aqueous cream with polypropylene glycol has led to the approval of acyclovir for the treatment of herpes labialis the reported results are contradictory. It is now said to be clear that a topically applied antiviral compound requires an aggressive, penetration-enhanced formulation in order to be able to permeate intact, undamaged stratum corneum immediately after the patient's first awareness of a new episode.

The use of aggressive enhancers damages the skin, causes irritation and sometimes contact allergy or other infections.

In order to provide an effective topical treatment of recurrent herpes infections, the first problem to be solved is to bring a sufficient amount of the active substance to penetrate the stratum corneum rapidly. The second problem is to bring the active substance to accumulate at the proper site, that is in the living epidermis, where the replication of herpesviruses takes place. Still another problem is the inflammation that follows upon virus multiplication and which is the causative agent of the symptoms associated with recurrent herpes virus infections. It would be desirable to combine foscarnet with an antiinflammatory substance in order to be able to treat the inflammation at the same time as the virus multiplication is inhibited. The formulation to be used must in addition be non-irritating to the skin and physically stable. This has been difficult to achieve with foscarnet due to the extremely polar character of the foscarnet molecule and the potential irritating properties when applied to the skin and the mucous membranes. It has also been a problem to find a carrier formulation in which foscarnet, which is water soluble, can be combined with less polar, insoluble antiinflammatory substances. There is today no efficient formulation for topical administration of foscarnet.

OUTLINE OF THE INVENTION

It has now, surprisingly, been found that the above described problems can be overcome by means of a pharmaceutical composition of the invention comprising foscarnet and an antiinflammatory glucocorticoid, in admixture with a carrier based on galactolipids and a polar solvent. The pharmaceutical composition comprises a combination of foscarnet and the glucocorticoid dispersed, dissolved or encapsulated in gels or other structures, such as liposomes, formed by double-chain bilayer-forming polar galactolipids and polar solvents. Such a composition is not irritating, penetrates the skin rapidly, provides an improved accumulation of foscarnet in the living epidermis, can sustain a high concentration of foscarnet, and is chemically and physically stable. The composition also provides an antiinflammatory agent to the skin or mucous membranes relieving the inflammatory symptoms. The galactolipids to be used with a polar solvent as a carrier in the composition of the invention provide a site-directed delivery of foscarnet to the living epidermis, thereby giving a maximum drug concentration at the site of disease with a minimum of adverse effects. Viscous formulations, suitable for topical administration, can be obtained without the addition of additional excipients.

Foscarnet, as used in this specification and claims, refers in addition to the hexahydrate of the trisodium salt of phosphonoformic acid, also to other pharmaceutically acceptable salts, esters or other derivates of phosphonoformic acid in hydrated or non hydrated form.

The antiinflammatory glucocorticoid suitable for the purposes of the present invention can be a naturally occurring or a synthetic topical glucocorticoid that is glucocorticosteroid. The glucocorticoids can be selected from any of the Group I-III glucocorticoids, according to a classification system for topical glucocorticoids used in the Nordic countries, corresponding to less potent, low or moderately potent glucocorticoids. Examples of glucocorticosteroids are alclometasone, amicinonide, beclomethasone, betamethasone, budesonide, ciclesonide, clobetasone, clocortolone, cloprednol, cortison, desonide, desoximethasone, dexamethasone, diflorosane, diflucortolone, difluprednate, fludrocortisone, fludroxycortid, flumethasone, flunisolide, fluocinolone acetonide, fluocinonide, fluocortin, fluocortolone, fluprednidene, fluticasone, halcinonide, halobetasol, halometasone, hydrocortisone, methylprednisolone, mometasone, paramethasone, prednisolone, prednicarbate, prednisone, prednylidene, rofleponide, tipredane and triamcinolone and their esters, salts and solvates, that is hydrates, where applicable.

Preferred glucocorticoids are hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide.

A preferred embodiment of the invention is a pharmaceutical composition comprising foscarnet and hydrocortisone; in another embodiment the pharmaceutical composition comprises foscarnet and budesonide.

Due to the herpesvirus-stimulating effects of glucocorticoids, care must be taken to define the optimal dose of the respective components. Too high a dose of the glucocorticoid might stimulate virus multiplication to an extent that can not be inhibited by the antiviral substance, that is foscarnet. With too low a dose the desired reduction of the symptoms of inflammation might not be achieved.

The mutual relationship between the two active substances will be different for different combinations of substances. The relative amount of foscarnet in a pharmaceutical composition according to the present invention can be within the range of 0.1–10% (w/w), preferably 0.3–5% (w/w). The antiinflammatory glucocorticoid concentration can be within the range of 0.005–3% (w/w) depending on the potency of the respective compound. A pharmaceutical composition containing a combination of foscarnet and hydrocortisone could comprise 0.1–5% foscarnet, preferably 0.3–3%, and 0.25–1% hydrocortisone.

The galactolipids in the composition of the invention consist of at least 50% digalactosyldiacylglycerols the remainder being other polar lipids.

In a preferred composition the galactolipid material consists of about 70–80% digalactosyldiacylglycerols and 20–30% other polar lipids.

In another preferred composition the galactolipid material consists of up to 100% digalactosyldiacylglycerols.

Two types of acylglycerols based on galactose are very common, that is monogalactosyldiacylglycerols and digalactosyldiacylglycerols. Commonly used abbreviations are MGDG and DGDG, respectively.

The digalactosyldiacylglycerols can be described by the general formula

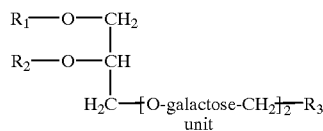

wherein $R_1$ and $R_2$ independently of each other are saturated or unsaturated fatty acid residues of 10–22 carbon atoms and 0–3 double bonds, or hydrogen; and $R_3$ is a hydroxyl or sulphonate group.

As preferred examples of fatty acid residues $R_1$ and $R_2$ can be mentioned naturally occurring fatty acyl groups, such as residues from the s aturated acids palmitic ($C_{15}H_{31}CO$; 16:0) and stearic acid ($C_{17}H_{35}CO$; 18:0); from the monounsaturated acid oleic acid ($C_{17}H_{33}CO$; 18:1); and from the polyunsaturated acids linoleic ($C_{17}H_{31}CO$; 18:2) and linolenic acid ($C_{17}H_{29}CO$; 18:3). The fatty acid residues can also include hydroxyacids linked to the glycerol moiety with their hydroxyl groups esterified by further fatty acids, so called estolides.

The specific proportions of the components of the galactolipid material are not critical to the present invention as long as the content of DGDG is at least 50%. For many applications, however, the maximum benefits are realised by a high content of DGDG, the most important bilayer-forming component.

The galactolipid material can be extracted from almost any kind of plant material. Preferred plant materials are seeds and kernels from grains and cereals, for instance wheat, rye, oats, corn, rice, millet and sesame. Oat groats as well as wheat gluten have a high lipid concentration and are therefore of advantage to use in the process of preparation. The digalactosyldiacylglycerols of the galactolipid material can, if applicable, also be of synthetic origin.

Isolation of galactolipids, especially DGDG, on a small scale, from plant sources is well-known and reported in the literature. Typically, mg to g amounts of plant lipid extracts are separated on thin-layer plates or silica columns with solvent systems containing chloroform, methanol and acetone.

The galactolipids can be obtained from plants on an industrial scale by conventional extraction and adsorption or displacement chromatography. The crude plant extract is loaded on a chromatography column containing an adsorbent as stationary phase, the non-polar lipids are eluted with a mixture of polar and non-polar solvents and the galactolipid material fraction, mainly containing DGDG, is then eluted with a more polar solvent mixture.

Addition of water or other polar solvents such as glycerol to the galactolipids to be used in the invention will result in the formation of lamellar lipid-water structures, often referred to as bilayer structures. The polar lipids of the invention can incorporate, that is swell, a large amount of water or aqueous solutions or other polar solvents. Due to the especially good intrinsic swelling properties of the galactolipids it is surprisingly easy to form liposomal dispersions without the presence of other chemical compounds than water, such as detergents or organic solvents. The process of making liposomes only involves the addition of water or a polar liquid in excess to the galactolipid material, swelling and gentle agitation or stirring. The dispersion obtained, consisting of multilamellar vesicles, that is liposomes, is extremely stable against aggregation and subsequent sedimentation.

The other polar lipids being part of the galactolipids is a mixture of different glyco- and phospholipids, such as MGDG and phosphatidylcholines. The composition depends on the starting material and process used for the manufacture of the galactolipids.

The polar solvent can be water and aqueous solutions, such as buffers and saline, or any other conventional solvent such as ethanol, glycerol, propylene glycol, polyethylene glycol, polypropylene glycol, glycofurol, methyl pyrrolidone, transcutol. Water is however the preferred solvent.

The pharmaceutical composition of the invention may also contain different additives or excipients which are pharmaceutically acceptable and compatible with the ingredients of the preparation. As examples of such additives can be mentioned thickening agents, preservatives, antioxidants, colorants, scent and taste agents, as well as other active substances, for instance vitamin A acid.

The pharmaceutical composition of the invention is suited for the prophylactic and/or curative treatment of herpesvirus infections in mammals including man, especially of HSV-1, HSV-2 and VZV, in the skin, the mucous membranes or eye. In a preferred embodiment the composition can be used for the treatment of recurrent herpesvirus infections. However, all herpesvirus infections, as well as infections by other viruses on which foscarnet has an effect, can be treated with the composition of the invention. Kaposi's sarcoma, KS, for instance, is a multifocal, polyclonal hyperplastic neoplasm, which is characterized by local growth and eventual metastasis. A new human herpes virus has recently been detected in KS lesions and has been proposed as being the causative agent. In clinical tests some patients have responded to intravenous treatment with foscarnet. Cutaneous KS lesions could be suitably treated by topical application.

The pharmaceutical composition can be administered topically, that is primarily to the intact skin, dermally, and to the eye, ocularly, but also to the mucosal surfaces, buccally, rectally and vaginally. Especially critical areas for treatment are where the intact skin borders the urogenital and digestive tract. A topical composition can be a cream, lotion, gel or ointment, which can be incorporated into a plaster, stick or pen.

An advantage with topical administration is that a viral cutaneous disease can be treated with much lower systemic exposure than in a standard intravenous treatment. It can, for instance, be estimated that an ordinary HSV recurrence typically is treated with about 100 mg of a topical formulation, which, if a 5% foscarnet cream is used, contains about 5 mg foscarnet. Previous research has shown that up to 5% of a topically applied amount of foscarnet might enter into the systemic circulation corresponding to 0.25 mg per application. This should be compared to the approved dosage of around 10 g a day in standard intravenous foscarnet treatment.

Topical administration of the pharmaceutical composition of the invention will bring about an improved delivery of the active substances to the site of virus replication, i.e. the living epidermis, while at the same time reducing the systemic distribution of foscarnet and relieving the symptoms of inflammation. In addition the degree of tissue irritation will be extensively reduced. The effects of said topical administration have resulted in a better pharmacological effect.

A method of prophylactic and/or curative treatment of herpes virus infections of the skin, mucous membranes or the eye in mammals including man, comprises topical administration, in combination or in sequence, of a therapeutically effective dose of foscarnet and of an antiinflammatory glucocorticoid. Said treatment comprises administration 1 to 10 times per day, preferably 3 to 4 times.

The curative treatment of recurrent infections should take place during the virus replication, preferably from the first appearance of prodromal symptoms and for a period of 3–4 days at least. It might be of advantage to apply the formulation during the whole episode, every second hour or ad lib. Lesions should be treated the same way. Prophylactic treatment could be an alternative in patients with regularly recurrent disease. In this case the formulation should be applied to the area where a recurrence is expected before the appearance of the first symptoms.

PHARMACEUTICAL COMPOSITIONS

EXAMPLE 1

Cream of Foscarnet 3%

Figure 1:
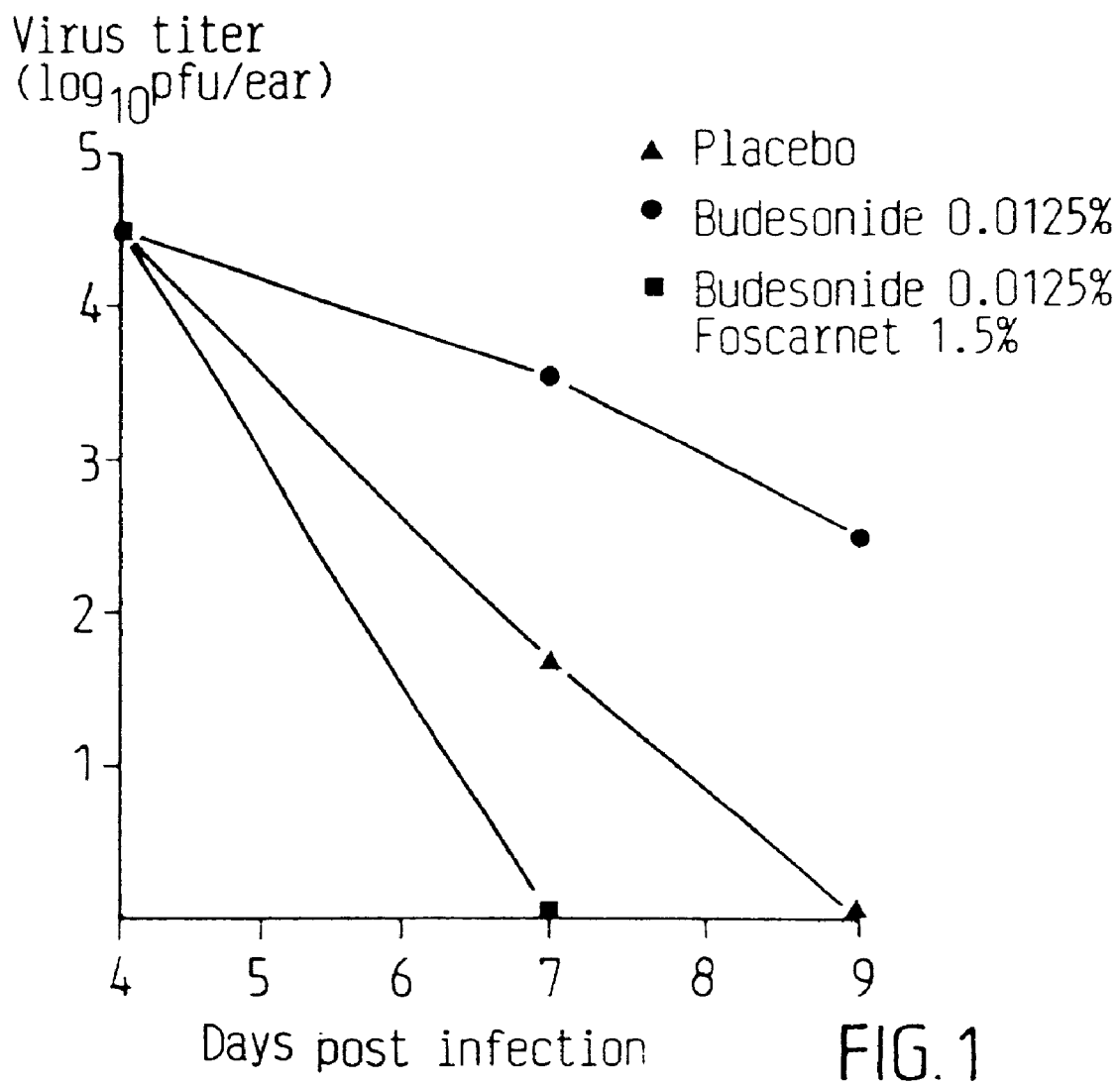
FIG. 1 Effects of topical treatment with budesonide and foscarnet+budesonide on days 4–7 after infection in comparison with placebo on mean HSV-titers in the pinna of neck-infected Balb/C mice (n=10) after adoptive transfer of immunity on day 2 after infection.

Foscarnet cream was prepared as described by Alenius, S. et al., "Therapeutic effects of foscarnet sodium and acyclovir on cutaneous infections due to herpes simplex virus type 1 in guinea pigs", J. Inf. Dis. 1982; 145:569–73). In the following said cream, with a content of 3% foscarnet and the composition as stated below, is referred to as Foscarnet Cream:

|  | Amount (mg) |
|---|---|
| Trisodium phosphonoformate hexahydrate | 30 |
| Polyoxyethylene fatty acid ester | 44 |
| Cetyl alcohol | 20 |
| Stearic acid | 20 |
| Paraffin liquid | 20 |
| Propylene glycol | 20 |
| Glycerol | 15 |
| Methyl p-hydroxybenzoate | 0.7 |
| Propyl p-hydroxybenzoate | 0.3 |
| Water | ad 1000 |

The cream base without foscarnet is used as the placebo cream. To the placebo cream can be added foscarnet in an amount of 3–30 mg as well as micronized hydrocortisone in an amount of 2.5–10 mg for the preparation of a cream of 0,3–3% foscarnet and 0.25–1% hydrocortisone.

EXAMPLE 2

Cream of Budesonide 0.0125% and Foscarnet 1.5%

By simple mixing of Foscarnet Cream and budesonide cream (0.025%, Preferid®, Gist-Brocades, The Netherlands) a combination cream was obtained having the following composition:

|  | Amount (mg) |
|---|---|
| Budesonide | 0.125 |
| Trisodium phosphonoformate hexahydrate | 15 |
| Sodium citrate | 0.6 |
| Citric acid | 0.3 |
| Sorbic acid | 0.3 |
| Cetostearyl alcohol | 30 |
| Paraffin liquid | 3 |
| Cetomacrogol 1000 | 6 |
| White soft paraffin | 15 |
| Arlatone (polyoxyethylene fatty acid ester) | 31 |
| Cetyl alcohol | 14 |
| Stearic acid | 14 |
| Mineral oil | 14 |
| Propylene glycol | 14 |
| Glycerol | 10.5 |
| Methyl p-hydroxybenzoate | 0.43 |
| Propyl p-hydroxybenzoate | 0.19 |
| Sodium hydroxide 2M* |  |
| Hydrochloric acid 2M* |  |
| Water | ad 1000 |

*For adjusting pH to 7–8

EXAMPLE 3

Cream of Foscarnet 1.5% and Lidocaine 1%

By simple mixing of Foscarnet Cream (3%) and lidocaine cream (2%, Xylocain®, Astra AB, Sweden) a combination cream was obtained having the following composition:

| | Amount(mg) |
|---|---|
| Lidocaine | 10 |
| Trisodium phosphonoformate hexahydrate | 15 |
| Miglyol 812 | 27.6 |
| Arlatone (polyoxyethylene fatty acid ester) | 44.2 |
| Carboxypolymethylene | 2 |
| Cetyl alcohol | 16 |
| Stearic acid | 16 |
| Mineral oil | 16 |
| Propylene glycol | 16 |
| Glycerol | 12 |
| Methyl p-hydroxybenzoate | 0.49 |
| Propyl p-hydroxybenzoate | 0.22 |
| Sodium hydroxide 2M* | |
| Hydrochloric acid 2M* | |
| Water purified | ad 1000 |

*For adjusting pH to 7–8

EXAMPLE 4

Cream of Hydrocortisone 1%

| | Amount (mg) |
|---|---|
| Hydrocortisone | 10 |
| Methyl p-hydroxybenzoate | 2.0 |
| Propyl p-hydroxybenzoate | 0.5 |
| Glycerol | 0.03 |
| Ethanol | 5 |
| Isopropylmyristate | 50 |
| Amphisol | 10 |
| Paraffin | 30 |
| Paraffin, liquid | 40 |
| Macrogol stearate | 100 |
| Cetyl alcohol | 50 |
| Water | ad 1000 |

This cream is commercially available as Hydrokortison kräm 1% ACO, Kabi Pharmacia AB, Sweden.

EXAMPLE 5

Cream of Foscarnet 1.75% and Hydrocortisone 0.5% in a Carrier Based on Galactolipids An antiviral and antiinflammatory formulation for topical administration was prepared as follows:

| | % w/w |
|---|---|
| Foscarnet | 1.74 |
| Hydrocortisone | 0.51 |
| Galactolipids | 29.0 |
| Polyethylene glycol 400 | 13.4 |
| Ethanol | 13.4 |
| Water | ad 100.0 |

Foscarnet (that is the trisodium salt of phosphonoformic acid, hexahydrate, from Astra AB, Sweden) was dissolved in water at a concentration of 4.00%. Hydrocortisone (Sigma Chemical Co., USA) was dissolved in a 1:1 (w/w) mixture of ethanol and PEG 400 at 70° C. Half of the amount of the galactolipids (galactolipids from oat grains having a lipid class composition of 70% DGDG and 30% other polar lipids including MGDG and phospholipids; the fatty acid residue composition, determined by GC as methyl esters, was 21% $C_{16:0}$ (palmitate), 3% $C_{18:3}$ (linolenate) and 5% residues from other fatty acids, prepared by Scotia LipidTeknik AB, Sweden) was added to the warm ethanol:PEG 400 solution until a homogenous dispersion was obtained. The lipid dispersion was heated to 70° C. and then the foscarnet solution was added during vigourous shaking. The rest of the galactolipids was added and the mixture was again subjected to high-shear mixing until a homogenous dispersion was obtained. After cooling to room temperature, a fine viscous lipid dispersion was obtained. This contained foscarnet dissolved in the polar solvent mixture and finely suspended hydrocortisone particles.

Liposomes and other bilayer structures formed from galactolipids have a number of advantages compared to the corresponding structures from phospholipids. Galactolipids incorporate more water than phospholipids, and galactolipids are also more resistant to hydrolysis than phospholipids, that is the galactolipid formulations are more chemically stable. The water swelling and the heat stability are demonstrated by the following tests.

Comparative formulations demonstrating water swelling properties

In order to formulate 2.4% foscarnet in a phospholipid, phosphatidylcholine from soybean, and get approximately the same viscosity as in the Formulations 4 and 5 above, it was necessary to use approximately 30 and 40% of phospholipid, respectively.

This shows that the galactolipids incorporate more water than phospholipids and that gels from galactolipids are more viscous. In order to obtain phospholipid gels of the same viscosity as a galactolipid gel, considerably higher amounts of phospholipids have to be used. This implies that a smaller amount of water can be used which in turn implies that a smaller amount of antiviral compound can be dissolved in the formulation.

BIOLOGICAL TESTS

Test 1. Skin permeation of foscarnet in galactolipids in vitro

In order to evaluate the influence of the formulations on the ability of foscarnet to penetrate the stratum corneum as well as to accumulate in the skin strata below stratum corneum an in vitro model was developed using intact skin from pig. The experimental model and the results are described below.

Skin from freshly slaughtered pigs was used. The underlying tissue was carefully removed with a scalpel and the skin was subsequently washed with 0.9% NaCl and dried. Finally, patches of skin were wrapped up in foil and freeze-stored at −28° C.

The diffusion cells were of glass consisting of a donor and a receiver part. The skin was placed between these two compartments and was secured by a metal clamp. The surface area of the donor compartment in contact with the formulation was 3.14 cm$^2$ and the volume was approximately 2 ml. The receiver compartment had a capacity of 28–29 ml and was supplied with a connecting tube to facilitate sampling and a jacket to control the temperature during the experiment.

The pig skin was thawed, dried and cut into an appropriate size. The skin patches were subsequently mounted on the diffusion cells. The receiver compartment was filled with 0.9% NaCl solution and care was taken to remove any bubbles of air between the underside of the skin and the solution in the receiver compartment. The solution was stirred continuously with a magnetic spinbar and kept at 37° C.

Three different 3% formulations of $^{14}$C-foscarnet were tested; in addition to Formulation A, containing 3% foscarnet, 40% galactolipids and the rest water, also Formulation B containing in addition to foscarnet the same amount of phospholipids, mainly sphingomyelin, instead of galactolipids, and water, and Formulation C being a conventional cream base containing in addition to foscarnet different enhancers such as polyoxyethylene fatty acid ester, stearic ester, propylene glycol and glycerol.

The different formulations were applied in an amount of 50–100 mg to the epidermal surface of different skin patches. The radioactivity of the formulations was determined at the beginning of each experiment. After 3 hours the skin patches were removed from the diffusion cells and a sample was taken from each receiver compartment. The sample was placed in a scintillation vial and assayed by scintillation spectrometry.

The skin patch was mounted on a board and a piece of adhesive tape was used to strip the skin. The amount of drug penetrating the deeper skin strata was assayed by slicing the remaining skin patch into thin sheets by means of a microtome. The sheets were placed in scintillation vials with Soluene 350 to dissolve over night. Scintillation cocktail was subsequently added and the samples were assayed by scintillation spectrometry.

The concentration of foscarnet upon application to each skin patch for each of the topical formulations was determined in the stratum corneum, in the skin strata below the stratum corneum and in the receiver compartment. The results are presented in the table below.

TABLE 1

Experimental data after 3 hours expressed as uptake in %

| Diffusion cell no. Formulation | Stratum corneum | Skin strata below s.c. | Receiver compartment |
| --- | --- | --- | --- |
| A  1 | 96.27 | 3.42 | 0.31 |
| 2 | 96.60 | 2.80 | 0.60 |
| 3 | 98.49 | 1.31 | 0.20 |
| mean value | 97.12 | 2.51 | 0.37 |
| B  1 | 99.51 | 0.41 | 0.08 |
| 2 | 99.07 | 0.86 | 0.07 |
| 3 | 98.95 | 0.94 | 0.11 |
| mean value | 99.18 | 0.74 | 0.09 |
| C  1 | 97.31 | 1.93 | 0.76 |
| 2 | 97.56 | 1.52 | 0.92 |
| 3 | 96.33 | 3.01 | 0.66 |
| mean value | 97.07 | 2.15 | 0.78 |

This indicates an improvement of the formulations of foscarnet in a galactolipid carrier over a conventional topical formulation for site-directed administration of foscarnet. From the above tests can be concluded that the skin distribution of foscarnet differs depending on the formulation used. A comparison between the conventional formulation C, and the galactolipid formulation A, is of particular interest. Three hours after the start of the penetration experiment similar amounts of foscarnet had penetrated the stratum corneum from Formulations A and C. With formulation A, however, the relatively rapid penetration of foscarnet into the skin is followed by a pronounced accumulation of the drug in the skin strata below stratum corneum, the region corresponding to the living epidermis, which is the site were the replication of the herpes virus takes place. It is also demonstrated that the phospholipid formulation B brings about a slower penetration of foscarnet through the stratum corneum.

Test 2. Effect of foscarnet and an antiinflammatory glucocorticoid on recurrent HSV-1 infection in vivo A primary herpes infection is characterized by a rapid and comparatively long-lasting phase of viral replication and a slower and less pronounced immune response causing only a low degree of inflammation. In a typical primary HSV infection shedding of virus continues for around 20 days, while in a recurrent infection virus shedding ceases after only 3 or 4 days (Whitley, R. J. and Gnann, J. W. in The Human Herpesviruses, Ed. Roizman et al., 1993). The common recurrent HSV and VZV infections are characterized by a strong and rapid immune response and inflammation causing clinical symptoms such as pain, redness and swelling. The immune response also rapidly limits the local virus replication, and typically 3–4 days after the first symptoms virus can no longer be isolated from lesions. In order to represent the clinical situation of recurrent HSV or VZV infections a new type of animal model has been used, as described below. Said model includes the induction of immune response in the animal before the administration of the composition to be tested.

Animal model for recurrent herpes infection

In the novel animal model, virus is inoculated in the neck of a mouse. The virus will then be transported through the nerves to the skin of the corresponding ear. This transport will take approximately 3–4 days. On day 2 the animals are given immune cells with reactivity against the infecting virus. Subsequently, when the virus arrives at the ear, the animal instantly mobilises an effective immune response against the virus, thus mimicking the clinical situation of a recurrent herpes infection.

Human HSV-1 ($2 \times 10^5$ plaque forming units, pfu, strain C42 or SC16) is inoculated into the neck of groups of 10–18 female in-bred Balb/C mice (16–18 g) as described by Kristofferson et al. ("Limited efficacy of inhibitors of herpes simplex virus DNA synthesis in murine models of recrudescent disease", J. Gen. Virol. 1988; 69:1157–66). The development of zosteriform spread infection is then recorded by daily inspection of the occurrence of lesions on the pinna and swelling of the ear.

The lesions are scored on a scale from 0 to 4 as follows:
0: no lesions on the ear
1: isolated zosteriform lesions on the ear
2: mild ulceration of zosteriform lesions on the ear
3: moderate ulceration of zosteriform lesions on the ear
4: severe ulceration of zosteriform lesions on the ear Swelling of the ear was assessed by measuring the thickness of the ears using an engineers micrometer, as described by Kristofferson et al. The titre of infectious virus in the ear was measured as described by Kristofferson et al, except that BHK (baby hamster kidney) cells were used in addition.

On day 2 after infection the animals are given adoptive transfer of immunity, ATI, against HSV-1 by intravenous injection of $2 \times 10^7$ lymph node cells into the tail. Said lymph node cells had been prepared by injecting HSV-1 ($10^5$ pfu, strain C42 or strain SC16) into the pinna of both ears of anaesthetisized female Balb/C mice (16–18 g). Seven days post infection the animals are sacrificed by cervical dislocation, the draining lymph nodes are removed, and a suspension of lymph node cells in phosphate buffered saline is prepared by means of a micromesh.

ATI decreases the virus titers in the ear of the infected animals, as well as the duration of virus shedding. However, ear swelling and lesion score of the ears is increased by ATI. Swelling is believed to correspond to inflammation and it is apparent that ATI worsens inflammation and lesion score even though virus is much more rapidly cleared.

On day 4 after the infection and for 4 days, a composition to be tested as to activity against recurrent herpes is distributed equally in an amount of approximately 25 mg of cream on each side of the ear, every 8 h.

Experiment 1. Test of combination creams of foscarnet and an antiinflammatory substance Budesonide and lidocaine were selected for testing as examples of antiinflammatory compounds.

The foscarnet cream Foscarnet Cream was prepared as described in Example 1. The cream base without drug was used as placebo.

The cream base described above was also nixed with budesonide cream (0.025%, Preferid®, Gist-Brocades, The Netherlands) to obtain suitable concentrations for treatment. For the experiments using a combination cream of foscarnet (1.5%) and budesonide (0.0125%), the formulation resulting from a mixing of the creams is described in Example 2.

A lidocaine cream (2%, Xylocain®, Astra AB, Sweden) was also mixed with the foscarnet cream and the resulting formulation of foscarnet (1.5%) and lidocaine (1%) is described in Example 3.

Foscarnet, the two antiinflammatory substances, as well as the two combination creams were tested in the animal model described, with ten animals in each group. The respective cream was applied day 4–7 after infection three times daily. The lesion score and ear thickness were recorded daily on days 4–12, 15 and 21 after infection and the mean cumulative values ±standard deviation calculated for said period. The results are given in Table 2 with the percent compared to placebo in parenthesis (values for placebo treated animals were set to 100%). Values significantly different from placebo-treated animals are indicated with an asterisk ($p=0.0001$).

TABLE 2

| Formulation | Compounded value ± s.d. (% of placebo) Lesion score | Compounded value ± s.d. (% of placebo) Ear thickness (mm) |
|---|---|---|
| Placebo | 9.2 ± 1.6 (100) | 3.6 ± 0.3 (100) |
| Foscarnet | 7.5 ± 2.5 (82) | 3.0 ± 0.4 (83) |
| Budesonide | 8.8 ± 1.8 (96) | 2.1 ± 0.4 (58)* |
| Lidocaine | 9 ± 2 (98) | 3.6 ± 0.3 (100) |
| Foscarnet + Budesonide | 5.3 ± 0.8 (58)* | 1.6 ± 0.1 (45)* |
| Foscarnet + Lidocaine | 9 ± 1.5 (98) | 3.5 ± 0.3 (97) |

Budesonide cream alone decreased the cumulative ear thickness to 58% of placebo-treated animals, while lidocaine cream had no effect. The combination of foscarnet and budesonide reduced ear thickness to 58%, compared to placebo. The combination of foscarnet and lidocaine had no effect on ear thickness or lesion score.

Treatment with a topical formulation o f budesonide increased the virus titers in the ears on day 7 and day 9 after infection between 100- and 1000-fold as compared with placebo treatment (FIG. 1). More specifically, the virus titers in the ears were dramatically reduced when the combination was used compared with placebo or budesonide cream (FIG. 1). No virus could be detected in the animals treated with the combination of foscarnet and budenoside on day 7 after infection.

Figure 2A:
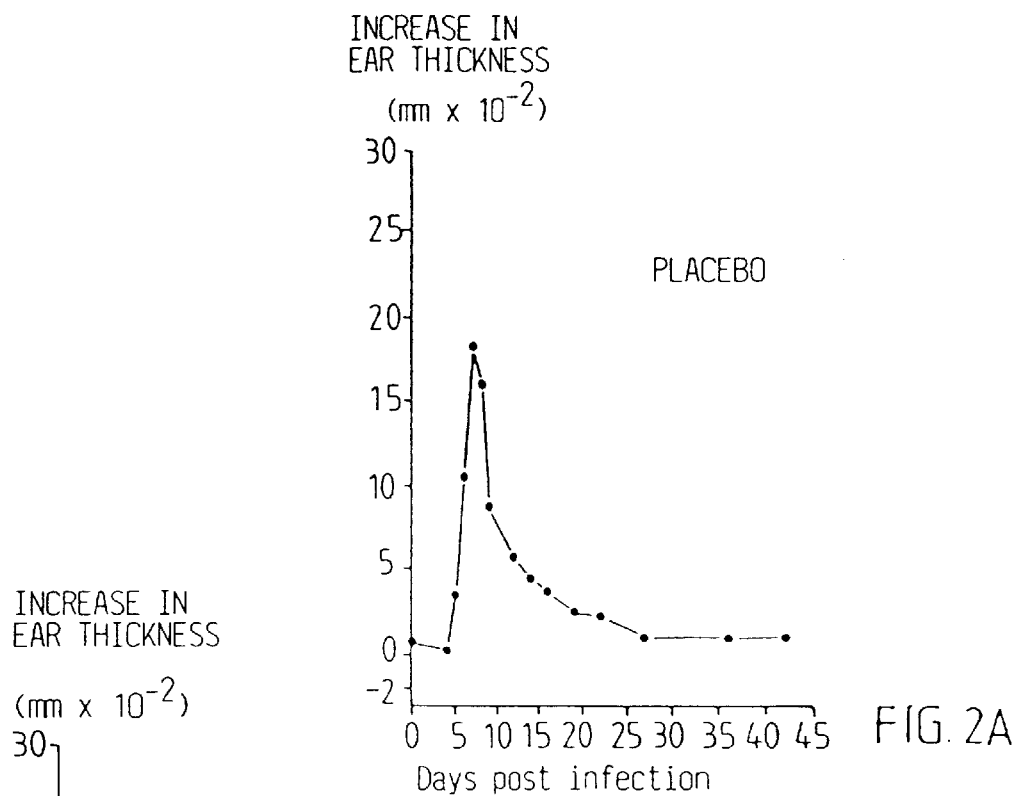
FIGS. 2A, 2B and 2C Effects of topical treatment with foscarnet and foscarnet+budesonide on days 4–7 after infection in comparison with placebo on median ear swelling of neck-infected Balb/C mice (n=12) after adoptive transfer of immunity on day 2 after infection.
Figure 2B:
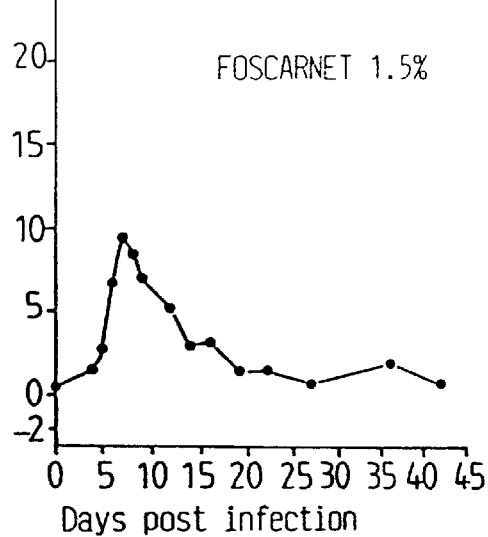
Figure 2C:
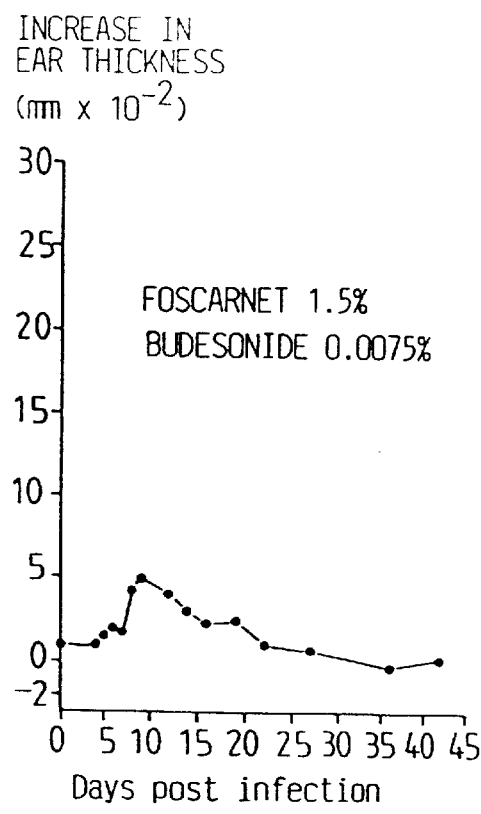

It was surprisingly found that the topical combination of foscarnet and budesonide was superior in efficacy when compared to foscarnet cream and budesonide cream when tested separately (FIGS. 1, 2). The results show that the combination of foscarnet and budesonide is superior to placebo, foscarnet cream alone and budesonide cream alone in terms of inflammation (as measured by ear thickness) and lesion score. This is especially surprising because budesonide cream alone stimulates virus growth compared to placebo.

Experiment 2. Sequencial test of foscarnet cream and an antiinflammatory cream

This experiment was performed to extend the results obtained in Experiment 1 using the same animal model with ten animals in each group. Mixing of foscarnet and an antiinflammatory substance into one composition might not result in a formulation having optimal penetration properties for the two active compounds. In this experiment the animals were treated with two different formulations 2 hours apart. First the foscarnet cream was applied and 2 hours later the antiinflammatory formulation. This was repeated three times daily during the treatment period (day 4–7 after infection).

The tested substances as well as the results obtained, that is cumulative lesion score and cumulative ear thickness measured as in Experiment 1, are shown in Table 3 with the percent compared to placebo in parenthesis (values for placebo treated animals were set to 100%). Values significantly different form placebo-treated animals are indicated with an asterisk ($p=0.0001$).

TABLE 3

| Active substance (% w/w) | Mean cumulative value ± s.d. (% of placebo) Lesion score | Mean cumulative value ± s.d. (% of placebo) Ear thickness |
|---|---|---|
| Placebo | 5.7 ± 1.3 (100) | 3.2 ± 0.3 (100) |
| Foscarnet | 4.8 ± 2.0 (84) | 2.8 ± 0.3 (88) |
| Foscarnet + Budesonide | 2.6 ± 1.0 (46)* | 1.9 ± 0.2 (59)* |
| Foscarnet + Hydrocortisone | 2.5 ± 1.1 (44)* | 1.7 ± 0.2 (53)* |
| Foscarnet + Lidocaine | 10.8 ± 1.5 (189) | 4.7 ± 0.4 (146)* |
| Foscarnet + Ketoprofen | 5.5 ± 1.4 (96) | 2.9 ± 0.3 (91) |

The following substances were tested: foscarnet (3%, Foscarnet Cream), budesonide (0.025%, Preferid®, Gist-Brocades, The Netherlands), hydrocortisone (1%, Hydrokortison kräm 1% ACO, Kabi Pharmacia AB, Sweden), lidocaine (5%, Xylocaine®, Astra AB) and ketoprofen (2.5%, Oruvail®, Rhone-Poulenc Rorer A/S, Denmark)

Foscarnet cream alone resulted in a small reduction in both lesion score and ear thickness in comparison to placebo which was not statistically significant. Foscarnet cream in combination with budesonide cream or with hydrocortisone cream was clearly superior to both foscarnet cream alone and placebo cream. Foscarnet cream in combination with budesonide cream reduced lesion score to 46% and ear thickness to 59% compared to placebo treated animals. Foscarnet cream in combination with hydrocortisone cream reduced lesion score to 44% and ear thickness to 53% compared to placebo treated animals. Foscarnet cream in combination with lidocaine cream worsened the lesion score and ear thickness to 189 and 146% of placebo-treated animals, respectively. Foscarnet cream in combination with ketoprofen cream had no effect on either lesion score or ear thickness. Two other NSAIDs, that is indomethacin (1%, Amuno® Gel, MSD Sharp & Dohme GmbH, Germany) and diclofenac (1.16%, Voltaren® Emulgel, Ciba-Geigy, GmbH, Germany) were also tested but the results could not be interpreted due to toxic side-effects. These side-effects were probably caused by systemic absorption of the NSADs in too high amounts.

As previously discussed, budesonide cream strongly increased the virus load in the animal model above compared with placebo (FIG. 1). This effect of budesonide is not beneficial for the treatment of herpes lesions. The virus titres in the ears of treated animals on day 7 after infection are shown in Table 4.

TABLE 4

| Treatment | Virus titre in the ear ($\log_{10}$pfu/ml) ± s.d. on d 7 |
|---|---|
| ATI−, placebo | 5.46 ± 0.35 |
| ATI+, placebo | 4.41 ± 0.09 |
| ATI+, foscarnet | 3.25 ± 0.49 |
| ATI+, foscarnet, hydrocortisone | 2.99 ± 0.28 |
| ATI+, foscarnet, ketoprofen | 2.62 ± 0.51 |
| ATI+, foscarnet, budesonide | 3.52 ± 0.16 |
| ATI+, foscarnet, lidocaine | 2.18 ± 0.51 |

Foscarnet cream alone reduced the virus titre on day 7 about tenfold compared to placebo-treated animals. Foscarnet cream in combination with hydrocortisone, ketoprofen, or lidocaine cream resulted in virus titres even lower than those in foscarnet-treated animals. Foscarnet cream in combination with budesonide resulted in virus titres on day 7 slightly higher than those of animals treated with foscarnet alone, but still nearly ten-fold lower than placebo-treated animals.

The results show that a combination of foscarnet with a glucocorticoid is clearly superior to combinations of foscarnet with a local anaesthetic or with ketoprofen as a nonsteroid anti-inflammatory drug (NSAID) with regard to inflammation (as measured by ear thickness) and lesion score. The results also show that a foscarnet combination including hydrocortisone—a less potent glucocorticoid—was superior to foscarnet combinations including budesonide—a more potent glucocorticoid—in terms of all the measured parameters, that is cumulative lesion score, cumulative ear thickness and mean virus titres.

Experiment 3. Test of a combination cream of foscarnet and hydrocortisone

This experiment was performed to extend the results of Experiment 2 by using foscarnet in combination with hydrocortisone. The same animal model with ten animals in each group was used. Animals were treated three times daily on days 4–7 after infection with foscarnet (3%, Foscarnet Cream, Example 1), hydrocortisone (1%, Hydrokortison, ACO, Kabi Pharmacia AB, Sweden, Example 4), and the combination cream, that is the formulation according to Example 5.

The substances tested and the results obtained (mean cumulative lesion score and mean cumulative ear thickness) are shown in Table 5, with the percent compared to placebo in parenthesis (values for placebo treated animals were set to 100%).

TABLE 5

| Active substance (% w/w) | Mean cumulative value ± s.d. (% of placebo) | |
|---|---|---|
| | lesion score | ear thickness (mm) |
| Placebo | 6.8 ± 1.1 (100) | 3.3 ± 0.4 (100) |
| Foscarnet | 7.3 ± 1.2 (107) | 3.3 ± 0.2 (98) |
| Hydrocortisone | 6.0 ± 1.3 (88) | 2.0 ± 0.2 (61)* |
| Foscarnet + hydrocortisone | 5.0 ± 1.2 (74) | 1.9 ± 0.1 (56)* |

Figure 3:
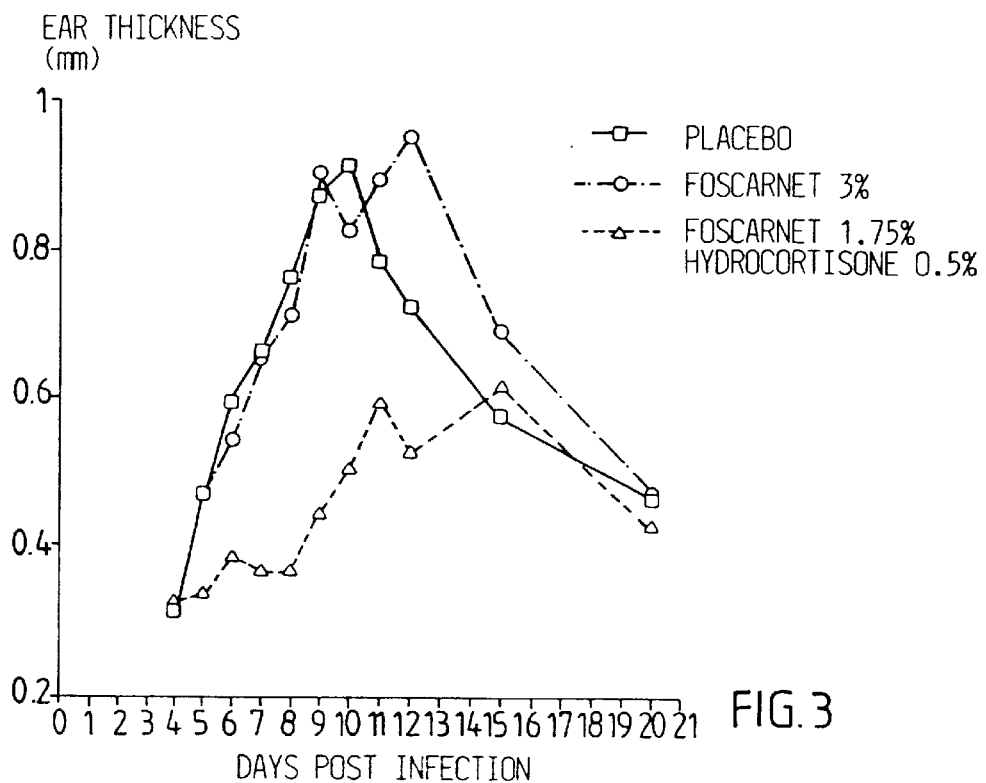
FIG. 3 Effects of topical treatment with foscarnet and foscarnet+hydrocortisone on days 4–7 after infection in comparison with placebo on mean ear thickness of neck-infected Balb/C mice (n=10) after adoptive transfer of immunity on day 2 after infection.

FIG. 3 shows the mean ear thickness on days 4–21 p.i. after treatment with placebo, 3% foscarnet or 1.75% foscarnet+0.5% hydrocortisone on days 4–7 p.i. The figure shows that foscarnet in combination with hydrocortisone was clearly superior in reducing the ear thickness to either foscarnet alone or placebo.

Figure 4:
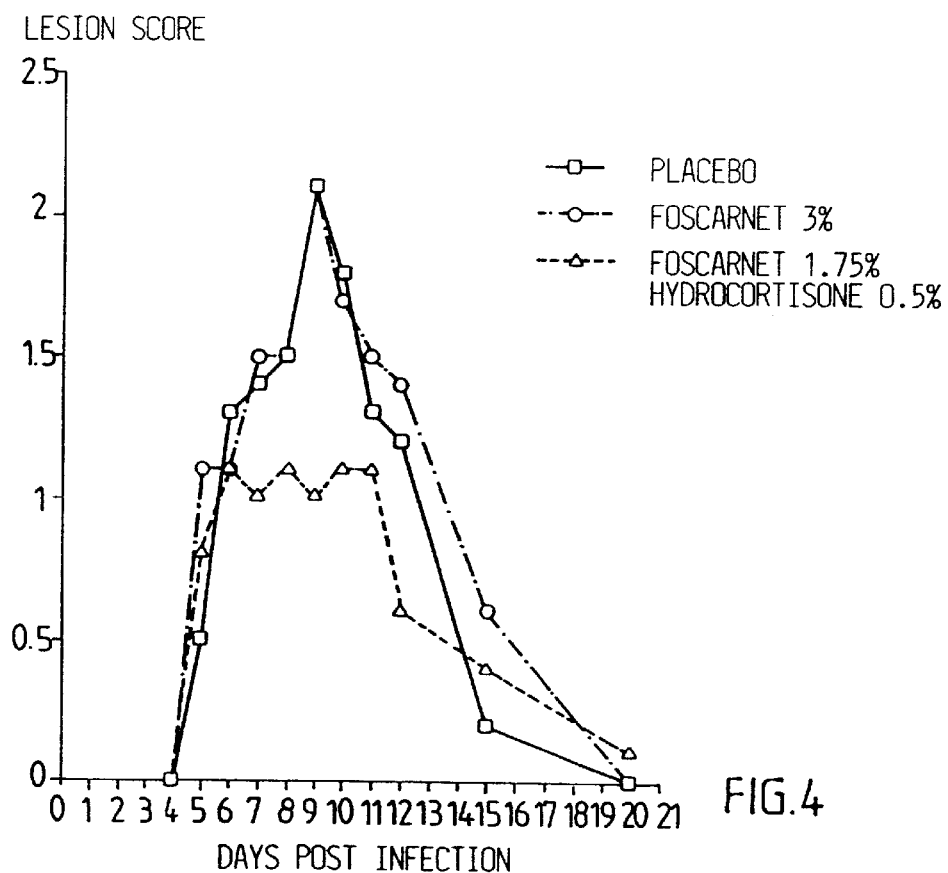
FIG. 4 Effects of topical treatment with foscarnet and foscarnet+hydrocortisone on days 4–7 after infection in comparison with placebo on mean lesion score of neck-infected Balb/C mice (n=1O) after adoptive transfer of immunity on day 2 after infection.

FIG. 4 shows the mean lesion score on days 4–21 p.i. after treatment with placebo, 3% foscarnet or 1.75% foscarnet+ 0.5% hydrocortisone on days 4–7 p.i. The figure shows that foscarnet in combination with hydrocortisone was clearly superior in reducing the lesion score to either foscarnet alone or placebo.

The results of the above experiments show that topical administration of a combination of foscarnet and an antiinflammatory glucocorticoid in addition to reducing the virus titer also reduces the inflammatory symptoms characteristic of a recurrent herpes infection as measured by ear thickness and lesion score.

Test 3. Cutaneous irritation in vivo

In order to evaluate the skin toxicity of the galactolipids of the invention the following test was performed.

Galactolipids (from oats, prepared by Scotia LipidTeknik AB, Sweden) were mixed with water for injection to a 10% gel and applied at a dose level of 0.5 ml per animal to the intact skin of 6 New Zealand White male rabbits and kept under semiocclusive bandage for 4 hours. A cutaneous examination for erythrema and oedema was then performed 1, 24, 48 and 72 hours after the removal of the bandage. Mean values were then calculated from the evaluation of the cutaneous lesions at 24, 48 and 72 h. The results are given in Table 6 below.

TABLE 6

| Cutaneous irritation in rabbits | | |
|---|---|---|
| | Erythema | Oedema |
| 24 h | 0 | 0 |
| 48 h | 0 | 0 |
| 72 h | 0 | 0 |

From this can be concluded that the application of a galactolipid gel does not provoke any noticeable irritation.

CONCLUSION

By means of a pharmaceutical composition of the present invention it is believed to be possible to combine the advantages of a combined antiviral and antiinflammatory effect with the improved penetration properties provided by the galactolipid carrier. A topical application of said composition to herpes virus infected areas will result in the prevention of or, in cases of onset of the outbreak of lesions, minimization of lesions caused by the herpesvirus and, consequently, in a faster healing.

We claim:

1. A pharmaceutical composition for topical administration comprising a combination of a therapeutically effective dose of foscarnet and an antiinflammatory glucocorticoid, in admixture with a carrier based on galactolipids and a polar solvent, wherein the galactolipids consist of at least 50% digalactosyldiacylglycerols, with the remainder being other polar lipids.

2. A pharmaceutical composition according to claim 1, wherein the antiinflammatory glucocorticoid is selected from the group consisting of hydrocortisone, alclometasone, desonide, fluprednidene, flumethasone, hydrocortisone butyrate, clobetasone, triamcinolone acetonide, betamethasone, budesonide, desoximethasone, diflorosane, fluocinolone, fluocortolone, fluticasone, methylprednisolone aceponate, mometasone and rofleponide.

3. A pharmaceutical composition according to claim 1, wherein the galactolipids consist of about 70%–80% digalactosyldiacylglycerols, and 20%–30% other polar lipids.

4. A pharmaceutical composition according to claim 1, wherein the galactolipids consist of up to 100% digalactosyldiacylglycerols.

5. A pharmaceutical composition according to claim 2, comprising a combination of an antivirally active amount of foscarnet and 0.005%–3% (w/w) of the antiinflammatory glucocorticoid.

6. A pharmaceutical composition according to claim 5, comprising a combination of foscarnet and hydrocortisone.

7. A pharmaceutical composition according to claim 5, comprising a combination of foscarnet and budesonide.

8. A pharmaceutical composition according to claim 6, wherein the foscarnet component is present in an amount of 0.1%–5% (w/w) and the hydrocortisone component is present in an amount of 0.25%–1% (w/w).

9. A pharmaceutical composition according to claim 8, wherein the foscarnet component is present in an amount of 0.3%–3% (w/w).

10. A cream, lotion, gel, ointment, plaster, stick or pen containing a pharmaceutical composition according to any one of claims 1, 2, 3–7, 8 and 9.

11. A pharmaceutical composition according to any one of claims 1, 2, 3–7, 8 and 9 for the prophylaxis and/or treatment of herpesvirus infections in mammals.

12. A pharmaceutical composition according to any one of claims 1, 2, 3–7, 8 and 9 for the treatment of recurring herpesvirus infections.

13. A method for the prophylaxis and/or treatment of herpesvirus infections of the skin, mucous membranes or eye in mammals, comprising topical administration, in combination or in sequence, of a therapeutically effective dose of foscarnet and of an antiinflammatory glucocorticoid.

14. A method according to claim 13, wherein the herpesvirus infection is a recurrent herpesvirus infection.

15. A method according to claim 13 or 14, wherein foscarnet and the glucocorticoid are administered 1 to 10 times per day.

16. A method according to claim 15, wherein foscarnet and the glucocorticoid are administered 3 to 4 times per day.

* * * * *